United States Patent [19]

Raynor

[11] Patent Number: 4,548,973
[45] Date of Patent: Oct. 22, 1985

[54] SELECTED 2,2,6,6-TETRAMETHYL-4-PIPERIDINYL DERIVATIVES AND THEIR USE AS LIGHT STABILIZERS

[75] Inventor: Robert J. Raynor, North Branford, Conn.

[73] Assignee: Olin Corporation, Cheshire, Conn.

[21] Appl. No.: 644,423

[22] Filed: Aug. 27, 1984

[51] Int. Cl.$^4$ .................. C08K 5/34; C07D 251/00
[52] U.S. Cl. .................. 524/102; 546/187; 546/193; 546/203; 424/59
[58] Field of Search .............. 524/102; 424/59; 546/187, 193, 203

[56] References Cited

U.S. PATENT DOCUMENTS

| | | | |
|---|---|---|---|
| 4,051,142 | 9/1977 | Carlson | 546/298 |
| 4,064,102 | 12/1977 | Hillard et al. | 524/99 |
| 4,115,101 | 9/1978 | Carlson | 546/288 |
| 4,115,396 | 9/1978 | Ursprung | 546/187 |

FOREIGN PATENT DOCUMENTS

| | | | |
|---|---|---|---|
| 332084 | 4/1972 | U.S.S.R. | 546/193 |
| 979442 | 12/1982 | U.S.S.R. | 524/102 |

*Primary Examiner*—John Kight
*Assistant Examiner*—Kriellion Morgan
*Attorney, Agent, or Firm*—William A. Simons; Thomas P. O'Day

[57] ABSTRACT

A 2,2,6,6-tetramethyl-4-piperidinyl derivative having a formula comprising:

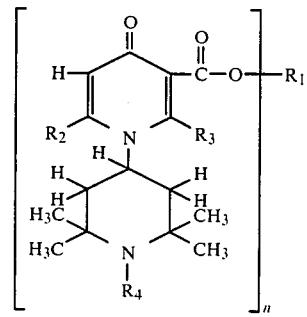

wherein $R_1$ is hydrogen, an alkyl or alkylene group having 1 to about 8 carbon atoms, or cycloalkyl or aryl groups having about 5 or 6 ring carbon atoms; $R_2$ and $R_3$ are individually selected from hydrogen, alkyl groups having 1 to about 8 carbon atoms, and cycloalkyl and aryl groups having about 5 or 6 ring carbon atoms; $R_4$ is selected from hydrogen and alkyl groups having 1 to about 8 carbon atoms; and n is either 1 or 2.

These compounds are useful as UV light stabilizers in plastics and cosmetics (e.g. sunscreens).

7 Claims, No Drawings

SELECTED 2,2,6,6-TETRAMETHYL-4-PIPERIDINYL DERIVATIVES AND THEIR USE AS LIGHT STABILIZERS

BACKGROUND OF THE INVENTION

1. Field of the Invention

This invention relates to selected 2,2,6,6-tetramethyl-4-piperidinyl derivatives as novel compositions of matter and their use as ultraviolet light stabilizers.

2. Discussion of the Prior Art

Ultraviolet (UV) radiation having wavelengths from about 280 to about 400 nm may cause the degradation of exposed organic matter such as plastics and will burn and/or induce tumors in human skin. To negate these undesirable actions, plastics and the like are protected by chemical additives called UV stabilizers and human skin and hair are protected by cosmetics containing UV stabilizers or sunscreens.

To be viable for commercial applications, a UV stabilizer should inhibit or dramatically retard degradation of organic material exposed to light by one or a combination of mechanisms such as the absorption of light energy or the entrapment of the destructive free radicals produced in the material by its interaction with light or oxygen or both. Absorbers should preferably have a strong ultraviolet light absorptivity at wave lengths between 280 and 400 nm. A light stabilizer should also be photostable by itself, be compatible with the substrate (e.g. plastic or cosmetic emulsion) in which it is used as an additive, be non-volatile at the high temperatures involved during incorporation and processing stages as well as during certain end uses, possess low color, be chemically inert, have low or no toxicity or skin sensitization/irritation properties, be non-mutagenic, and be stable to the environments experienced during its processing and application. Furthermore, for human sunscreen use, it is also desirable that the UV stabilizer be relatively insoluble in water.

Accordingly, it is an object of the present invention to provide a novel class of UV light stabilizer compounds.

A specific object of this invention is to provide a novel class of UV light stabilizer compounds which may be used to stabilize ultraviolet degradable organic compositions, particularly plastics, against deterioration resulting from the exposure to such UV radiation.

Another specific object is to provide a novel class of UV light stabilizer compounds which may be used in human cosmetic products such as sunscreens, hair dyes and hair tinting compositions to prevent or retard UV radiation from penetrating the human skin or hair.

These and other objects and features of the invention will be made apparent from the following more particular description of the invention.

BRIEF SUMMARY OF THE INVENTION

The present invention, therefore, is directed to 2,2,6,6-tetramethyl-4-piperidinyl derivatives having the formula (I):

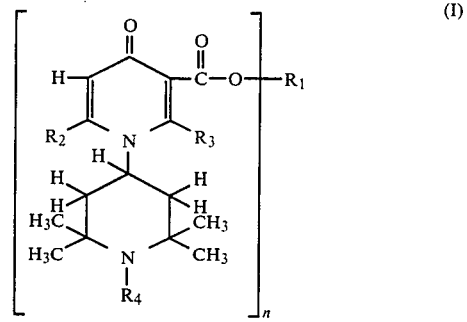

wherein $R_1$ is hydrogen, an alkyl or alkylene group having 1 to about 8 carbon atoms, or cycloalkyl or aryl groups having about 5 or 6 ring carbon atoms; $R_2$ and $R_3$ are individually selected from hydrogen, alkyl groups having 1 to about 8 carbon atoms, and cycloalkyl and aryl groups having about 5 or 6 ring carbon atoms; $R_4$ is selected from hydrogen and alkyl groups having 1 to about 8 carbon atoms; and n is either 1 or 2. When $n=2$, $R_1$ is a difunctional moiety such as an alkylene group (e.g. methylene or ethylene group) or an arylene group (e.g. a phenylene group).

Also, the present invention is directed to organic compositions susceptible to ultraviolet degradation being stabilized against such degradation with an effective stabilizing amount of a 2,2,6,6-tetramethyl-4-piperidinyl derivative having formula (I) above.

Still further, the present invention is directed to a process for stabilizing an organic composition, such as a plastic, a coating or the like, susceptible to ultraviolet degradation comprising incorporating into said organic composition an effective stabilizing amount of a 2,2,6,6-tetramethyl-4-piperidinyl derivative having fromula (I), above.

Furthermore, the present invention is directed to human sunscreen compositions which effectively prevent or retard UV light from penetrating human skin or hair, said sunscreen compositions comprising an effective screening amount of a 2,2,6,6-tetramethyl-4-piperidinyl derivative having formula (I) above.

And even further, the present invention is directed to a process for substantially screening out UV light from human skin or hair comprising applying a sunscreen composition on said skin or hair to prevent or retard UV light from penetrating to said skin or hair, said sunscreen composition comprising an effective screening amount of a 2,2,6,6-tetramethyl-4-piperidinyl derivative of formula (I), above.

DETAILED DESCRIPTION

The present substituted lutidone carboxylic acid derivatives ($R_1=H$) of 2,2,6,6-tetramethylpiperidine may be made by reacting the appropriate dehydroacetic acid with 4-amino-2,2,6,6-tertramethylpiperidine, preferably with a solvent such as a toluene, at a reaction temperature from about 40° to about 200° C. This reaction is illustrated by the formation of 1,4-dihydro-2,6-dimethyl-4-oxo-1-(2,2,6,6-tetramethyl-4-piperidinyl)-3-pyridinecarboxylic acid by the reaction of 1 mole of dehydroacetic acid with 1 mole of 4-amino-2,2,6,6-tetramethylpiperidine as shown in the following equation (A):

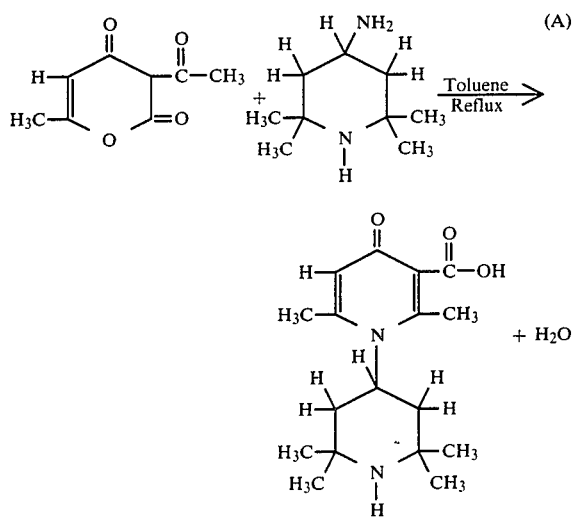

These substituted lutidone carboxylic acids (i.e. $R_1 = H$) may be directly esterified ($R_1$ changed to a carbon containing group) by any of several procedures. These may include the following:

(1) The acid moiety may be converted to its sodium salt by treatment with caustic (NaOH) and the resulting sodium salt in turn may be reacted with an alkyl chlorosulfite ($R_1OSOCl$) and then heated to 100°–150° C. to yield the corresponding alkyl ester.

(2) The methyl ester ($R_1 = CH_3$) may be prepared by the action of diazomethane ($CH_2N_2$) on the lutidone carboxylic acid in ether.

Alternatively, the esters of pyrone carboxylic acids may be used (in place of dehydroacetic acid) for reaction with 4-amino-2,2,6,6-tetramethylpiperidine to give the $R_1$ esters directly.

When $R_2$ and $R_3$ are hydrogen or alkyl groups other than methyl, then other means of their preparation may be employed. In those cases where $R_2 = R_3$, these compounds may be prepared by the cyclization of an acyl acetic acid ethyl ester under the influence of a basic material such as sodium bicarbonate, followed by its isomerization in 85% by weight $H_2SO_4$ to form the corresponding pyrone carboxylic acid. This acid is then reacted with the 2,2,6,6-tetramethylpiperidine to form the desired product, according to the above-noted procedure. In those cases where $R_2$ is not the same as $R_3$, then these compounds may be made by the reaction of 4-hydroxy-6-alkyl-2-pyrone with an acid chloride ($R_3COCl$) in the presence of trifluoroacetic acid catalyst to form the corresponding 3-alkylcarbonyl-4-hydroxy-2-pyrone. This compound may be isomerized to the corresponding pyrone carboxylic acid. The pyrone acid or its ester is then reacted with the 2,2,6,6-tetramethylpiperidine to form the desired product.

The hydrogen on the nitrogen atom of the tetramethylpiperidine portion of the compound made by the reaction of (A), above, may be replaced by an alkyl group either directly or indirectly. Direct replacement would include treatment of the piperidine with a reactive alkyl halide such as an alkyl bromide in the presence of a strong base such as sodium bicarbonate or reaction with an alkyl tosylate. Alternatively an indirect reaction sequence can be employed. Rather than using 4-amino-2,2,6,6-tetramethylpiperidine, a corresponding N-alkyl-substituted 2,2,6,6-tetramethylpiperidine may be used in its place.

It should be recognized the present invention is not dependent upon any particular reaction conditions or precursors to form the compounds of formula (I), above. Advantageously and preferably, the reaction is carried out with a 1:1 mole ratio of the dehydroacetic acid precursor to the piperidine precursor in the presence of a suitable inert solvent. Preferred solvents include benzene, toluene, xylene, diphenyl ether, glycol ethers, hexane and the like. However, the use of a solvent is only desirable, but not necessary. The reaction temperature and time will both depend upon many factors including the specific reactants used. In most situations, reaction temperatures may advantageously be from about 40° C. to about 200° C. and reaction times from about 15 minutes to about 300 minutes or more may be preferred. The product may be recovered from the reaction mixture by any conventional means such as filtration, extraction or the like. The product may be further purified by conventional means such as recrystallization in an inert solvent, fractional distillation, or the like.

The compounds of the present invention are believed to possess a combination of properties which make them advantageous as UV stabilizers. These desirable properties include their white or near-white color, their nonvolatility, their stability under normal storage conditions, their insolubility in water but solubility in certain organic solvents, their exceptionally strong maximum absorptivity of UV light from about 280 to about 320 nm wavelengths.

The preferred compounds of the present invention are those where $R_1$ = hydrogen or a lower alkyl group having 1 to 4 carbon atoms; $R_2 = R_3$ = hydrogen and a lower alkyl group having 1 to 4 carbon atoms; $R_4$ = hydrogen or a lower alkyl group having 1 to 4 carbon atoms; and n=1. The most preferred compound is where $R_1$ = H; $R_2 = R_3 = CH_3$; $R_4$ = H; and n=1.

Also in accordance with the present invention, the compounds of formula (I) above may be utilized as effective ultraviolet stabilizers for UV degradable organic material or in human sunscreen compositions. In practicing the use as a UV stabilizer for such organic materials, an effective stabilizing amount of one or more of these compounds is incorporated into the organic composition susceptible to UV degradation. In practicing the use as a UV stabilizer in human sunscreen composition, an effective screening amount of one or more compounds of formula (I) is incorporated into the sunscreen composition which is applied to human skin or hair. It is to be understood that the terms "effective stabilizing amount" and "effective screening amount" as used in the specification and claims wherein is intended to include any amount that will prevent or retard UV radiation from either degrading the organic material incorporated therein or penetrating the human skin or hair, respectively. Of course, these amounts may be constantly changing because of possible variations in many parameters. Generally, amounts from about 0.01% to about 10%, by weight, based on the weight of the organic or carrier material to which they are added. While a detectable amount of stabilization or screening may be obtained with amounts less than 0.01%, this amount of stabilization or screening would be of little practical utility in a commercial application. Moreover, while amounts greater than 10% by weight provide effective ultraviolet stability and screening, such concentrations are undesirable because of cost and the deleterious effect which such concentrations may have on the mechanical properties of the organic composition in which the UV stabilizer is incorporated. Preferably, the stabilizer is used in an amount of from about 0.1% to about 3% by weight.

Possible organic materials which are susceptible to UV degradation and which may have the compounds of formula (I) incorporated therein as UV stabilizers include organic polymers (both thermoplastic and thermosetting polymers). Wholly synthetic polymers such as addition polymers, condensation polymers and condensation polymers crosslinked by addition polymerization may be aided with these UV stabilizers. Natural polymers such as polysaccharides, rubber and proteins may also be aided. Also, chemically modified polymers may be employed as substrates as well as other substances such as natural and synthetic light-sensitive waxes, fats and oils; emulsions which contain light-sensitive fatty substances or the abovementioned polymers.

Exemplary lists of these polymers and other substances are shown in U.S. Pat. No. 4,127,586, which issued to Rody et al on Nov. 28, 1978, and U.S. Pat. No. 3,936,418, which issued to Pond et al on Feb. 3, 1976. Both of these U.S. Patents are incorporated herein by reference in their entireties.

Any suitable carrier material which is presently used for human sunscreen compositions may have the compounds of formula (I) incorporated therein. Examples of this carrier material for sunscreens include emollients or emulsions of conventional cosmetic chemicals known in the art.

Such organic compositions and sunscreen compositions may contain further additives, pigments, colorants, stabilizers and the like. These may include antioxidants, other UV stabilizers and sunscreens, metal deactivators, phosphites, lubricants, fillers and the like.

These compounds of formula (I) may be incorporated into these organic compositions or sunscreen compositions by any convention blending technique such as melt-blending, mixing or the like. Alternatively, they may add on the surface of such materials or affixed thereto by means of a gel or the like.

The following examples further illustrate the present invention. All parts and percentages employed therein are by weight unless otherwise indicated.

EXAMPLE 1

Preparation of
1,4-Dihydro-2,6-dimethyl-4-oxo-1-(2,2,6,6-tetramethyl-4-piperidinyl)3-pyridinecarboxylic acid A 1-liter, 3-neck, round-bottom flask was equipped with a mechanical stirrer, thermometer, and a Dean-Stark water trap topped with a water cooled condenser. The flask was charged with a mixture of 80.5 g (0.479 mol) dehydroacetic acid, 75.0 g (0.479 mol) 4-amino-2,2,6,6-tetramethylpiperidine, and 600 ml toluene. The stirred mixture in the flask was heated to the boiling point by means of an oil bath and the water formed during the reaction was collected in the trap. After 6 hours of reflux a total of 7.0 ml water had been collected and the flask and its contents cooled to room temperature. The mixture deposited crystals on standing which were collected by vacuum filtration. Reduction of volume of toluene in the filtrate caused a deposit of a second crop of crystals. The combined crystals were recrystallized from a 65/35 mixture of hexane/benzene to give 111 g (75.6%) of a white to colorless crystalline solid (M.P. 174° C.). The chemical structure and purity of these crystals were verified by mass spectroscopy, nuclear magnetic resonance spectroscopy; and by elemental analysis.

| | Elemental Analysis: | |
|---|---|---|
| | % Calculated | % Found |
| C | 66.64 | 66.71 |
| H | 8.55 | 8.54 |
| N | 9.14 | 9.14 |

EXAMPLE 2

Proposed Preparation of
1,4-Dihydro-2,6-dimethyl-4-oxo-1-(2,2,6,6-tetramethyl-4-piperidinyl)-3-pyridinecarboxylic acid, methyl ester The subject compound's precursor, methyl 2,6-dimethyl-4-oxopyran-3-carboxylate may be prepared as described in U.S. Pat. No. 4,051,142, which issued to Carlson. The procedure to be used is as follows.

A 1-liter, 3-neck, round-bottom flask is equipped with a mechanical stirrer, a thermometer, and a Soxhlet extractor topped with a water cooled condenser. The extractor is filled with 125 g of type 3A molecular sieves and the flask with 80.5 g (0.479 mole) dehydroacetic acid, 500 ml methyl alcohol, and 20 g of concentrated (96%) sulfuric acid. The stirred mixture in the flask is heated to the boiling point by means of an oil bath. The resulting vapor is condensed and allowed to flow through the molecular sieves and returned to the flask. This process is continued for 24 hours. The cooled mixture is then diluted with 250 ml of methylene chloride and neutralized with aqueous caustic. Water is added to the mixture and the methylene chloride layer is separated from the resulting two-phase system. The water layer is extracted twice more with 250 ml amounts of methylene chloride. The combined methylene chloride extracts are washed twice with water, dried over magnesium sulfate, filtered free of solids, and the solvent is removed on a rotary evaporator. The residue is then subjected to vacuum distillation through a 10 inch Vigreaux column yielding 48 g of methyl 2,6-dimethyl-4-oxopyran-3-carboxylate boiling between 130°–136° C. at 1.0 mm pressure.

A 500 ml, 3-neck, round-bottom flask is equipped with a mechanical stirrer, thermometer and a Dean-Stark water trap topped with a water cooled condenser. The flask is charged with a mixture of 45.5 g (0.25 moles) of the methyl 2,6-dimethyl-4-oxopyran-3-carboxylate prepared as described above, 39.1 g (0.25 m) 4-amino-2,2,6,6-tetramethylpiperidine, and 300 ml toluene. The stirred mixture in the flask is heated to boiling by means of an oil bath and the water formed during the reaction is collected in the trap. After 4 hours of reflux a total of 3.8 ml water is collected and the flask and its contents are cooled to room temperature. The toluene is removed by means of a rotary evaporator. On standing and cooling the residue deposits crystals of the title product which are further purified by fractional crystallization.

EXAMPLE 3

Proposed Preparation of
1,4-Dihydro-2,6-diphenyl-4-oxo-1(2,2,6,6-tetramethyl-4-piperidinyl)-3-pyridinecarboxylic acid A 250 ml round-bottom flask is equipped with a mechanical stirrer, thermometer, and a distillation head and condenser set up to remove distillate. The flask is charged with 100 g (0.52 moles) ethyl benzoylacetate and 0.075 g sodium bicarbonate. The flask and its contents are heated by means of an oil bath over a period of about 5 hours at temperature from ambient to a maximum of 200° C. while the ethanol formed is continuously removed. Unreacted ethyl benzoylacetate is removed by vaccum distillation. The residue consisting of crude 3-benzoyl-6-phenyl-2H-pyran-2,4-(3H)-dione is then heated at 80°–85° C. with 500 g of 85% sulfuric acid for 4 hours. This mixture is poured into 1 liter of ice-water and the water extracted three times with 150 ml portions of chloroform. The combined chloroform extracts are stripped of volatiles on a rotary evaporator and the residue of 2,6-diphenyl-4-oxopyran-3-carboxylic acid isolated by fractional crystallization. A toluene solution of this pyrone is then treated with an equal molar quantity of 4-amino-2,2,6,6-tetramethylpiperidine and refluxed with removal of water by means of a Dean-Stark trap. When water has ceased to separate, the toluene is removed on a rotary evaporator and the residue cooled and treated with hexane to promote crystallization of the crude product. The product is further purified by fractional crystallization.

EXAMPLE 4

Proposed Preparation of
1,4-Dihydro-2,6-dimethyl-4-oxo-1-(1,2,2,6,6-Pentamethyl-4-piperidinyl)-3-pyridinecarboxylic acid A sample of 1,2,2,6,6-pentamethyl-4-piperidone is prepared by known procedures from phorone and methyl amine. Treatment of this piperidone with hydroxyl amine to produce the corresponding oxime followed by reduction of the oxime by metallic sodium in alcohol is employed to prepare 4-amino-1,2,2,6,6-pentamethyl piperidine.

A 500 ml, 3 neck, round-bottom flask is equipped with a mechanical stirrer, thermometer, and a Dean-Stark water trap topped with a water cooled condenser. The flask is charged with a mixture of 42.5 g (0.25 moles) of 4-amino-1,2,2,6,6-pentamethyl piperidine, 42.0 g (0.25 moles) dehydroacetic acid, and 300 ml toluene. The stirred mixture in the flask is heated to boiling by means of an oil bath and the water formed during the reaction is collected in the trap. After 4-5 hours of reflux, water has ceased to separate and the flask and its contents are cooled to room temperature. The toluene is removed by means of a rotary evaporator and after standing and cooling the resulting residue deposits crystals of the title product. These crystals are further purified by fractional crystallization.

The ultraviolet light absorptivity properties of the compound of Example 1 was measured by means of a spectrophotometer and is given in Table I. A comparison is also given for 2(2H-benzotriazol-2-yl)-p-cresol (TINUVIN P) and para-aminobenzoic acid (PABA), which are well known UV stabilizers. These data indicate that the compound of the present invention is a very good ultraviolet absorber. The photostability of the compound of Example 1 was also measured by subjecting a solution of this compound to the UV radiation produced by a 450 watt medium pressure mercury lamp at 13° C. in a Hanovia photochemical apparatus and periodically determining its absorbance by means of a spectrophotometer. The data as shown in Table II indicate excellent photostability.

TABLE I

| Example | Wave Length (λ) max. | Absorptivity (1/g. cm)[1] | Molar Absorptivity[2] |
| --- | --- | --- | --- |
| 1 | 314 | 62.8 | 19,242 |
| 2(2H—benzotriazol-2-yl)-p-cresol | 340 | 70 | 15,750 |
| para-aminobenzoic acid | 290 | 132.8 | 18,200 |

[1]Measured on a Perkin-Elmer spectrophotometer, Model No. 330.

Absorptivity (a) equals $\frac{A}{bc}$ where A = absorbance (also called optical density) and is an observed (experimentally determined) value; b = cell size; and c = concentration of compound in solvent

[2]Molar Absorptivity = absorptivity (a) times molecular weight.

TABLE II

| Photolysis of 1,4-Dihydro-1,6-dimethyl-4-oxo-1-(2,2,6,6-tetramethyl-4-piperidinyl)-3-pyridinecarboxylic acid | |
| --- | --- |
| Time (hrs.) | Absorbance (A) at 314 nm |
| 0 | 0.642 |
| 0.3 | 0.665 |
| 2.0 | 0.660 |
| 4.0 | 0.630 |
| 5.0 | 0.611 |

Test as Plastic Additive

Various test sample formulations were prepared by dry blending several UV stabilizers and an antioxidant[1] into unstabilized powdered polypropylene[2]. The final formulation contained 1% by weight UV stabilizer, 0.1% antioxidant and the balance powdered polypropylene. The antioxidant was used to stabilize the polypropylene during the high temperature extursion. These mixtures were extruded into 5, 25 and 50 mil thick films in a ¾ inch plastic-making extruder at 250° C. These films were then tested in a Q-U-V Accelerated Weather Tester[3] in accordance with ASTM G53-77 standard procedures.

[1] Irganox 1010 antioxidant made by Ciba-Geigy Corporation.
[2] Pro-fax 6501 polypropylene mady by Hercules Inc.
[3] made by Q-Panel Co.

As can be seen from the following Table (III), the ability of the compound of Example 1 to protect polypropylene against degradation under simulated weathering conditions is comparable to and/or exceeds that of well known, commercially available light stabilizers.

TABLE III

| Comparative Test Results Q-U-V Accelerated Weathering Tester | | | |
| --- | --- | --- | --- |
| | Days to Failure | | |
| UV Stabilizer | 5 Mil Films | 25 Mil Sheet | 50 Mil Sheet |
| None | 3 | 9 | 9 |
| Cyanamid Cyasorb 1084 | 16 | 25 | 25 |
| Ciba-Geigy Tinuvin 327 | 11 | 20 | 20 |
| Ciba-Geigy Tinuvin 770 | 38 | 108 | 114 |
| Example 1 | — | 90 | 110 |

What is claimed is:

1. A 2,2,6,6-tetramethyl-4-piperidinyl derivative having a formula comprising:

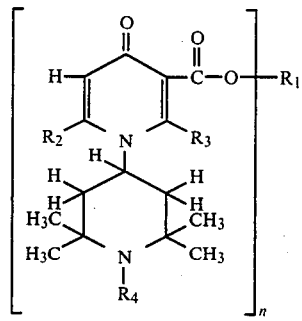

wherein $R_1$ is hydrogen, an alkyl or alkylene group having 1 to about 8 carbon atoms, or cycloalkyl or aryl groups having about 5 or 6 ring carbon atoms; $R_2$ and $R_3$ are individually selected from hydrogen, alkyl groups having 1 to about 8 carbon atoms, and cycloalkyl and aryl groups having about 5 or 6 ring carbon atoms; $R_4$ is selected from hydrogen and alkyl groups having 1 to about 8 carbon atoms; and n is either 1 or 2.

2. The derivative of claim 1 wherein $R_1 = H$; $R_2$ and $R_3 = CH_3$; $R_4 = H$; and $n = 1$.

3. An organic composition susceptible to ultraviolet degradation stabilized against such degradation with an effective stabilizing amount of a 2,2,6,6-tetramethyl-4-piperidinyl derivative having the formula:

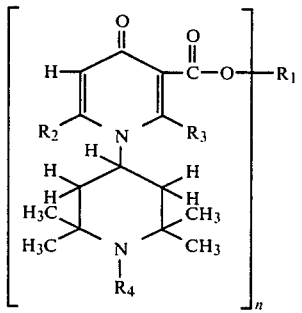

wherein $R_1$ is hydrogen, an alkyl or alkylene group having 1 to about 8 carbon atoms, or cycloalkyl or aryl groups having about 5 or 6 ring carbon atoms; $R_2$ and $R_3$ are individually selected from hydrogen, alkyl groups having 1 to about 8 carbon atoms, and cycloalkyl and aryl groups having about 5 or 6 ring carbon atoms; $R_4$ is selected from hydrogen and alkyl groups having 1 to about 8 carbon atoms; and n is either 1 or 2.

4. The organic composition of claim 3 wherein said organic composition is an organic polymer.

5. A process for stabilizing organic compositions susceptible to ultraviolet degradation comprising incorporating into said organic composition an effective stabilizing amount of 2,2,6,6-tetramethyl-4-piperidinyl derivative having the formula:

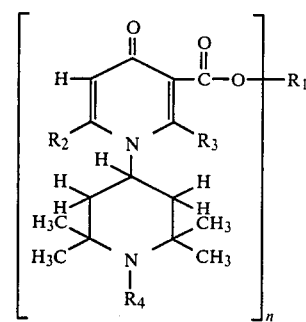

wherein $R_1$ is hydrogen, an alkyl or alkylene group having 1 to about 8 carbon atoms, or cycloalkyl or aryl groups having about 5 or 6 ring carbon atoms; $R_2$ and $R_3$ are individually selected from hydrogen, alkyl groups having 1 to about 8 carbon atoms, and cycloalkyl and aryl groups having about 5 or 6 ring carbon atoms; $R_4$ is selected from hydrogen and alkyl groups having 1 to about 8 carbon atoms; and n is either 1 or 2.

6. In a sunscreen composition which effectively prevents UV light from penetrating to human skin or hair; wherein the improvement comprises an effective screening amount of 2,2,6,6-tetramethyl-4-piperidinyl derivative having the formula:

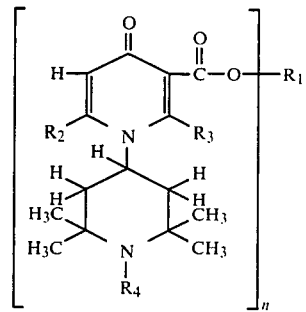

wherein $R_1$ is hydrogen, an alkyl or alkylene group having 1 to about 8 carbon atoms, or cycloalkyl or aryl groups having about 5 or 6 ring carbon atoms; $R_2$ and $R_3$ are individually selected from hydrogen, alkyl groups having 1 to about 8 carbon atoms, and cycloalkyl and aryl groups having about 5 or 6 ring carbon atoms; $R_4$ is selected from hydrogen and alkyl groups having 1 to about 8 carbon atoms; an n is either 1 or 2.

7. In a process for substantially screening out UV light from human skin or hair which comprises applying a sunscreen composition on said skin or hair to prevent or retard UV light from penetrating to said skin or hair; the improvement which comprises said sunscreen composition comprising an effective screening amount of 2,2,6,6-tetramethyl-4-piperidinyl derivative having the formula:

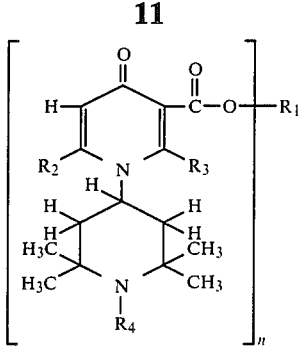

wherein $R_1$ is hydrogen, an alkyl or alkylene group having 1 to about 8 carbon atoms, or a cycloalkyl or aryl groups having about 5 or 6 ring carbon atoms; $R_2$ and $R_3$ are individually selected from hydrogen, an alkyl group having 1 to about 8 carbon atoms, and a cycloalkyl and aryl group having about 5 or 6 ring carbon atoms; $R_4$ is selected from hydrogen and an alkyl group having 1 to about 8 carbon atoms; and n is either 1 or 2.

* * * * *